(12) United States Patent
Saoudi et al.

(10) Patent No.: US 7,831,016 B2
(45) Date of Patent: Nov. 9, 2010

(54) RADIATION DOSIMETRY APPARATUS AND METHOD, AND DOSIMETER FOR USE THEREIN

(75) Inventors: Abdelhamid Saoudi, King Abdulaziz Medical City (SA); Joanna Ewa Cygler, Ottawa (CA); Robert William Ashton, Nepean (CA)

(73) Assignee: Best Medical Canada

( * ) Notice: Subject to any disclaimer, the term of this patent is extended or adjusted under 35 U.S.C. 154(b) by 282 days.

(21) Appl. No.: 12/073,189

(22) Filed: Mar. 3, 2008

(65) Prior Publication Data
US 2009/0010390 A1 Jan. 8, 2009

Related U.S. Application Data

(60) Provisional application No. 60/904,169, filed on Mar. 1, 2007.

(51) Int. Cl.
*A61N 5/10* (2006.01)
(52) U.S. Cl. ...................................... 378/65
(58) Field of Classification Search ............ 250/370.07; 378/65, 97
See application file for complete search history.

(56) References Cited

U.S. PATENT DOCUMENTS

| 5,558,091 | A | * | 9/1996 | Acker et al. | 600/424 |
|---|---|---|---|---|---|
| 2001/0032933 | A1 | * | 10/2001 | Thomson et al. | 250/370.01 |
| 2005/0213706 | A1 | * | 9/2005 | Raymond et al. | 378/97 |
| 2006/0002519 | A1 | * | 1/2006 | Jenkins et al. | 378/207 |
| 2006/0067474 | A1 | * | 3/2006 | Schmitt | 378/102 |
| 2006/0153341 | A1 | * | 7/2006 | Guyonnet et al. | 378/207 |
| 2007/0058778 | A1 | * | 3/2007 | Coleman et al. | 378/65 |
| 2007/0161884 | A1 | * | 7/2007 | Black et al. | 600/407 |
| 2008/0212737 | A1 | * | 9/2008 | D'Souza et al. | 378/65 |

* cited by examiner

*Primary Examiner*—Chih-Cheng G Kao
(74) *Attorney, Agent, or Firm*—Oneal R. Mistry (57) ABSTRACT

In order to overcome or at least mitigate difficulties in compensating for movement of the target, for example a tumour during radiotherapy, a dosimetry apparatus and method embodying the present invention employ a dosimeter having at least one radiation detector and at least one magnetic position sensor located a predetermined distance apart. Radiation level readings from the radiation detector and position readings from the position sensor are monitored and correlated, conveniently according to time, to obtain the position of the radiation detector when a particular radiation level was detected.

36 Claims, 4 Drawing Sheets

RADIATION DOSIMETRY APPARATUS AND METHOD, AND DOSIMETER FOR USE THEREIN

CROSS REFERENCE TO RELATED APPLICATION

This application claims priority from U.S. Provisional patent application No. 60/904,169 filed Mar. 1, 2007; the entire contents of this prior application are incorporated herein by reference.

TECHNICAL FIELD

This invention relates to radiation dosimetry apparatus and methods for measuring radiation, and to dosimeters for use therein. The invention is especially, but not exclusively, applicable to radiation dosimetry apparatus and methods and dosimeters for monitoring levels of ionizing radiation during medical procedures, such as radiation therapy as used for the treatment of, for example, tumours.

BACKGROUND OF THE INVENTION

When ionizing radiation is being used, it is usually important to confine the radiation to the target volume and avoid irradiating surrounding material. This is especially important when using radiation therapy to treat tumours. So-called conformal radiotherapy seeks to deliver high radiation doses to the tumor volume and at the same time provide maximum sparing of healthy neighbouring tissues, which entails high dose gradients (steep dose falloff) outside the tumor volume. Examples of such radiotherapy techniques are Intensity Modulated Radiation Therapy (IMRT), Intra-Operative Radiotherapy (IORT) and Brachytherapy.

Commercially available external beam radiation therapy machines which can deliver an accurate and precise radiation dose to a well-defined volume in space include, for example, linear accelerator (LINAC) based machines which have been adapted to use Intensity Modulated Radiation Therapy (IMT). Commercial radiosurgery and/or radiotherapy systems presently are marketed under the brand names Trilogy® (Varian Medical Systems, Inc.), Axess® (Elekta, Inc.), X-Knife® (Radionics, Inc.), Novalis® (BrainLAB, Inc.), CyberKnife® (Accuray, Inc.) and Tomotherapy, and may use CT or MRI imaging in order to conform the radiation three-dimensionally to the target volume and minimize irradiation of surrounding healthy tissue.

The precision of delivery is affected during treatment by the inherent limitation of the imaging procedure used to delineate tumour boundary and the physician's skill in defining gross tumour volume; the latter varying from one physician to another. The dose delivery accuracy and position accuracy may also be affected by the accuracy of the dose calculation algorithm, the daily patient setup errors and mechanical positioning tolerances of the treatment machine. These effects individually or combined, will contribute to reduced accuracy and precision in the delivery of the radiation.

Further inaccuracy may be caused by movement of the target, i.e., the tumour, before and/or during therapy. The lung or breast may move significant distances because of respiration and cardiac functions. The prostate may move, as a result not only of respiration but also, for example, normal functioning of the rectum and bladder. Although feasible, it would be undesirable for the physician to compensate by increasing the irradiated volume to ensure that the entire tumour is treated, because that would likely result in increased damage to neighbouring healthy tissue.

It has been proposed to improve accuracy by tracking movement of the target volume during and/or between radiation therapy sessions. According to United States published patent application number 2006/0093089, the entire contents of both of which are incorporated herein by reference, imaging techniques, such as X-ray, CT, MRI and ultrasound, which are used to align the target volume with fiducial marks upon the patient and with the isocentre of the radiation beam equipment, are not particularly suitable for monitoring movement of the target volume caused by bodily functions. US 2006/0093089 discloses, instead, inserting one or more leadless (AC magnetic) markers into the target volume and using a panel of AC magnetic sources and sensors to determine the location of each marker in a reference frame external to the patient.

It is not enough, however, merely to ensure that the radiation is applied to the right location. It is equally important to ensure that the amount of radiation, i.e., the dose, received at a particular location is correct, according to the treatment plan. Usually, during a typical radiation therapy session, the radiation dose actually received at specified locations is measured by means of dosimeter detectors positioned in or near the target volume. The radiation level measured by a particular dosimeter detector may be affected by its proximity to an interface between two heterogeneous media and/or its proximity to a large dose gradient where dose measurements are difficult to perform accurately. For example, one might wish to irradiate the whole of the prostate gland without exposing the neighbouring rectum or urethra to damaging radiation. This imposes a need for a large transition in the radiation level over a relatively short distance. Even a slight body movement might result in the boundary of the prostate gland shifting and the rectum or urethra being subjected to an unacceptable level of radiation. Consequently, the accurate determination of the position of the detector at the time a particular radiation dose is being given is very important.

Usually, the radiation detectors are carefully positioned at the desired measurement locations before the session commences, perhaps by means of one of the above-mentioned imaging techniques and with reference to fiducial marks, for example gold markers or tattoos upon the patient, or fixed body parts. U.S. Pat. No. 6,614,025 (Thomson), commonly owned with the present invention, discloses a dosimeter having several radiation detectors referenced to a radio-opaque marker which facilitates the use of such imaging to determine the position of each radiation detector relative to the fiducial marks during the pre-treatment procedure. Nevertheless, the procedure is quite complex and provides the position at only one point in time. If the above-described movements caused by bodily functions displace a radiation detector during the actual radiation session, the dose read by the detector, when retrieved, may not be the dose actually received at the prescribed position.

The above-mentioned imaging techniques are not generally suitable for monitoring the location of a radiation detector during a radiation session. More particularly, to monitor the position of the radiation detectors while taking account of organ movement would require repeated or even continuous imaging, since a single image would not be sufficient to correlate the organ movement and the position of the detector(s). Also, it is not desirable to expose the patient to ionizing radiation in addition to that to which the patient must be exposed during therapy. Nor is it usually convenient to use an X-ray machine or other imaging machine at the same time as the radiation therapy machine.

When Brachytherapy is used instead of external beam radiation therapy, especially to treat prostate cancer, changes in the shape and size of the target volume may occur between the volume study being carried out and the radioactive isotope seeds actually being implanted. Changes also may occur during the actual implantation procedure as a result of edema and variable prostate texture causing movement in response to needle insertion and seed migration after insertion. It is particularly important, therefore, to ensure that the dose delivered to the prostate is measured accurately. As before, real-time imaging to track movement of the radiation detector(s) is not practical.

SUMMARY OF INVENTION

The present invention seeks to overcome or at least mitigate the afore-mentioned limitations of known dosimetry apparatus and methods and, to this end, provides a dosimeter system and method employing a dosimeter having at least one radiation detector and at least one position sensor located a predetermined distance apart, and means for reading both the detector and the sensor to obtain both a radiation level detected by the radiation detector and the position of the radiation detector when that radiation level was detected.

According to one aspect of the invention, dosimetry apparatus for determining radiation dosage applied to a target during a radiotherapy/surgery session comprises a dosimeter configured for location in or adjacent said target during said session, output means coupled to the dosimeter, and magnetic field generating means, the dosimeter comprising at least one radiation detector means and at least one magnetic field sensor means located a predetermined distance apart, the magnetic field generator being operable to establish a magnetic field encompassing said magnetic field sensor during/throughout said radiotherapy/surgery session, the radiation detector means being arranged to sense ionizing radiation and provide a corresponding radiation level signal, the magnetic field sensor means being responsive to movement thereof relative to the magnetic field to provide a corresponding position sensor signal, and the output means being arranged to process both the radiation level signal and the position sensor signal and, in dependence thereupon, provide an indication of both the level of a radiation dose detected by the radiation detector and the location at which the dose was measured.

The position sensor may comprise a plurality of coils having axes extending in different directions whose movement relative to said magnetic field generates the corresponding sensor signals, the output means including processing means for processing the sensor signals to obtain direction and distance of movement of the sensor.

According to a second aspect of the invention there is provided a method of measuring radiation dose and the position at which the dose was measured using a dosimeter having a radiation detector and a magnetic position sensor located a predetermined distance apart, and magnetic field generating and detecting means, the method comprising the steps of:

positioning the radiation detector and magnetic position sensor at a known distance relative to a fiducial marker and establishing the position of the sensor as a datum, positioning the radiation detector at a desired position at which to measure radiation dose during radiation therapy, determining the position of the magnetic field sensor, measuring the radiation dose acquired by the radiation detector over a prescribed period of time, and correlating the measured radiation dose with the position of the magnetic sensor thereby to determine the position at which the dose was measured.

In preferred embodiments of either aspect of the invention, the measured radiation doses and positions of the magnetic sensor are each measured with respect to time and said correlating of measured radiation doses and position is based upon time.

The dose and its position may be measured at intervals throughout a planned therapy session and the treatment plan adjusted to compensate for variations of the measured dose at a particular position and the planned dose.

Additionally, signals from the sensor and detector may be correlated (time and position synchronized) with physiological signals from a patient undergoing therapy and/or with other equipment, and generating gating signals, in order to further monitor and/or control the dose delivered to the target. For example, embodiments of the invention may be used with so-called "gating" techniques and with CT or other imaging systems According to a third aspect of the invention, there is provided a dosimeter having a radiation detector and a magnetic position sensor located a predetermined distance apart and means for connecting respective outputs ports of the detector and the sensor to external reading means for extracting signals from the detector and sensor for processing to determine a radiation level measured by the detector and its position.

Thus, dosimetry apparatus and a method are provided employing a dosimeter having at least one radiation detector and at least one magnetic position sensor located a predetermined distance apart, so that radiation level readings from the radiation detector and position readings from the position sensor may be monitored and correlated, conveniently according to time, to obtain the position of the radiation detector when a particular radiation level was detected.

BRIEF DESCRIPTION OF DRAWINGS

Various features, objects and advantages of the invention will become apparent from the following description of preferred embodiments of the invention which are described, by way of example only, with reference to the accompanying drawings, in which.

In the drawings, identical or corresponding elements in the different Figures have the same reference numeral.

DETAILED DESCRIPTION OF PREFERRED EMBODIMENTS

Figure 1:
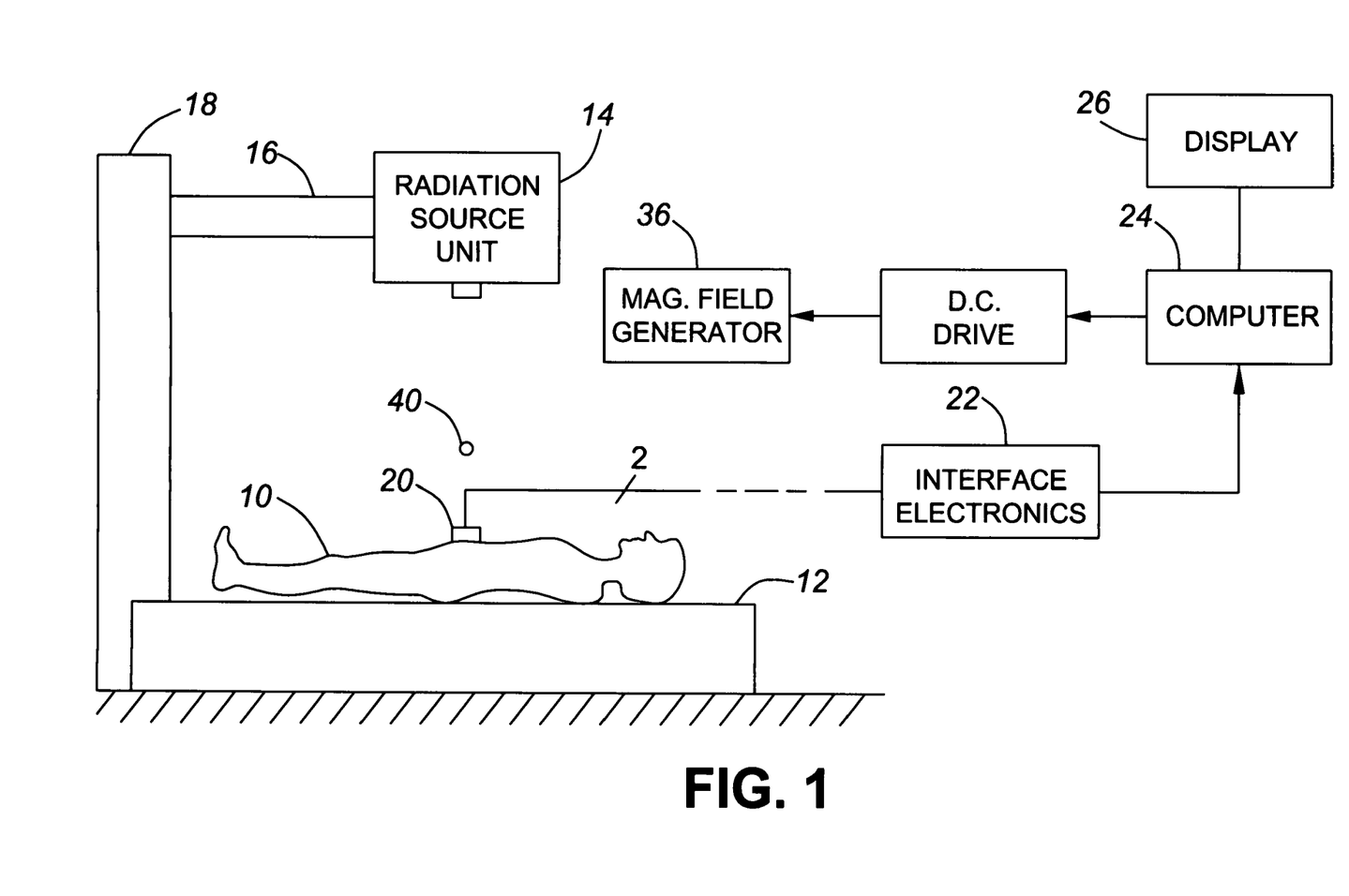
FIG. 1 is a schematic diagram of radiation therapy/surgery equipment and a patient undergoing radiation therapy/surgery.

FIG. 1 illustrates a patient 10 lying on a table 12 beneath a radiation source unit 14 carried by a gantry 16 extending from a support 18 of a known kind of radiation therapy machine which irradiates a target volume on or in the patient's body in known manner. Such radiation therapy or surgery equipment is well known to those skilled in this art and so will not be described in detail herein. FIG. 1 also illustrates dosimetry apparatus for monitoring the radiation, which comprises a dosimeter 20 shown, for ease of depiction, mounted upon the patient's abdomen, and having at least one radiation detector for detecting radiation levels over a prescribed time period and providing corresponding readings or doses by way of an electronic interface unit 22, sometimes called a reader, which converts the radiation level readings into a digital format, and sends them to a computer 24 for analysis and display of the radiation dose on a display device 26, e.g., a computer monitor. The computer 24 may be a microprocessor integrated with the interface electronics 22 or a separate personal computer.

For details of known radiation dosimeters and associated electronic interface units of this kind, the reader is directed to U.S. Pat. Nos. 6,614,025, 6,650,930, 6,172,368, 5,117,113 and 4,678,916, the contents of each of which are incorporated herein by reference. A dosimeter 20 embodying the present invention, however, differs from those disclosed in these cited patents because it includes both a radiation detector 28 and a magnetic position sensor 30.

Figures 2A, 2B:
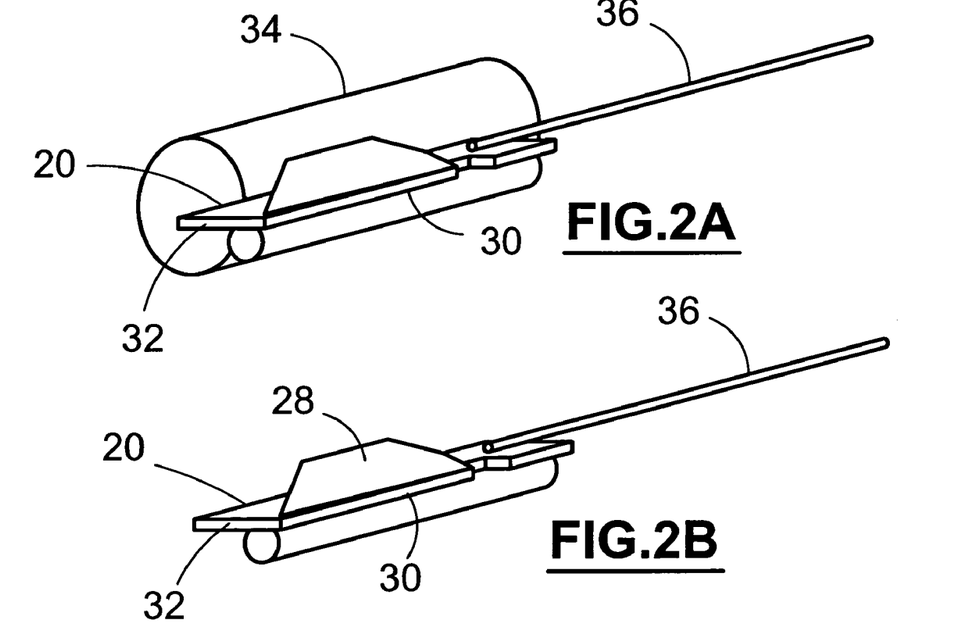
FIGS. 2A and 2B are schematic perspective views of a dosimeter having a radiation detector and a magnetic position sensor.

In the specific example illustrated in FIGS. 2A and 2B, the detector 28 and sensor 30 are mounted upon opposite sides of a substrate 32 at the end of the dosimeter 20 and surrounded by encapsulation 34. The radiation detector 28 and magnetic sensor 30 each have multiple electrical connections to the interface unit 22 by way of respective conductors (not shown) of a thin, narrow flexible printed circuit strip 36, the distal end of which is connected to the interface unit 22. The three-dimensional spatial relationship between the radiation detector 28 and the magnetic sensor 30 is predetermined accurately during manufacture because this spatial relationship must be taken into account when determining the position of the radiation detector 28 based upon information about the position of the magnetic sensor 30. It is envisaged, however, that predetermination of this spatial relationship might not be confined to the factory but might be done later, possibly even in the hospital.

Referring again to FIG. 1, the dosimetry apparatus also comprises a magnetic field generator (or transmitter) 36 coupled to the computer 24 by a drive unit 38 which causes the generator 36 to establish a magnetic field having a desired field strength. During a radiotherapy/surgery session, with the dosimeter 20 disposed adjacent a target to be irradiated, the generator 36 will be positioned such that the magnetic field strength at the magnetic field sensor 30 will be sufficient for the magnetic sensor 30 to provide an adequate signal level to the electronic interface unit 22. To this end, the magnetic field generator 36 will usually be located as close as possible to the target, but not so close as to be affected adversely by the radiation. In FIG. 1, the magnetic field generator 36 is shown above the patient but, in practice, might conveniently be located on the table 12, either adjacent or beneath the patient 10, typically in the vicinity of the target (volume). For example, where the target volume is the prostate gland, the generator 36 might be located next to or beneath the patient's hip.

In preferred embodiments of the invention, the magnetic field sensor 30 comprises a magnetic field tracking device of the kind which provides the position in three-dimensional space, or with up to six degree of freedom. For example, a sensor 30 may comprise a plurality of coils having axes extending in different directions whose movement generates the corresponding sensor signals (e.g. x, y, z coordinates and orientation angle) with respect to a DC magnetic field.

A magnetic tracking system of the kind marketed by under the trademark "microBIRD" by Ascension Technology Corporation of Burlington, Vt. 05402, USA, suitably adapted, would be particularly suitable because its magnetic field sensor is able to fit inside a catheter. Likewise, MOSFET radiation detectors marketed by Best Medical Canada Ltd. would be particularly suitable because they could fit inside the same catheter. (Of course, in some applications, no catheter is needed).

During setting up of the equipment, the magnetic tracking system, comprising the magnetic field sensor 30 and the magnetic field generator 36, will be initialized by positioning the transmitter 36 and the sensor 30 at respective predetermined positions, in the case of the sensor 30 on or a certain distance from a fiducial mark(s) on the patient, and the sensor 30 output readings zero-ed or recorded. Thereafter, movement of the magnetic field sensor 30 relative to the magnetic transmitter 36 and, more importantly, relative to the fiducial mark, can be tracked. This fiducial mark may conveniently be the same mark, often a visual reference mark, that is provided on the patient at a precise location relative to the target volume using CT or MRI imaging during a pre-treatment procedure, and used immediately prior to the radiotherapy/surgery session to position the patient relative to the isocenter 40 of the radiation therapy/surgery equipment. The radiation detector 28 will be "zero-ed" in the usual way at the beginning of the session.

With the patient correctly positioned, and the position monitoring and radiation monitoring systems initialized, the radiation therapy session will proceed. As the magnetic sensor 30 moves, the interface 22 will process the information received from the position sensor 30 to track the changes in the position of the magnetic field sensor 30 with respect to time. Using standard computer protocol, the interface 22 will send information regarding the position of the sensor 30 to the computer 24 which, taking into account the spatial relationship between the radiation detector 28 and the magnetic sensor 30 established during manufacture, determines the position of the radiation detector 30. It should be noted that the intervals at which radiation level readings and position sensor 30 readings are taken may be selected according to the nature of the expected target movement. For example, the intervals might be milliseconds or seconds.

During or after the radiation therapy session, the interface electronics unit 22 will read the dosage signals from the radiation detector 28, and the time, and convey them to the computer 24 which will use the time to reference the magnetic sensor 30 position at that time and hence, taking into account the spatial relationship, determine the detector 28 position at the time and record not only the radiation dosage readings but also the position of the detector 28 at the time. It should be noted that, if the dosimeter has several radiation detectors, as disclosed in U.S. Pat. No. 6,614,025, the spatial position of each of them relative to the magnetic sensor will be predetermined during manufacture (though perhaps adjustable later) and the computer 24 will be programmed with that information, enabling it to correlate the radiation dose read by each radiation detector with the position of that particular detector.

The radiation level signal usually will be sampled or monitored at intervals appropriate to the accumulated radiation levels. The position signal also may be sampled or monitored at intervals, which may be different from those at which the radiation level signal is sampled/monitored. Such sampling advantageously may reduce data storage requirements. However, it would be possible to monitor the position signal substantially continuously, for example analog or sampled at a high rate, and use the time at which radiation dose was read to sample the position signal. It is also envisaged, however, that the radiation level signal and the position signal could be sampled/monitored simultaneously. Also, it may be desirable to accumulate position and radiation level data for later analysis, perhaps to evaluate the effectiveness of the radiation therapy.

The computer 24 may process and display the radiation readings and their respective positions separately, leaving the operator to make the correlation between such actual doses and positions and those set out in the treatment plan. It is envisaged, however, that the computer 24 could be programmed to correlate the position and radiation dose readings with the treatment plan and display the information using a graphics display to identify the location on an image or representation of part or all of the patient's body, conveniently of the kind disclosed in U.S. Pat. No. 6,650,930 (Ding) which is commonly owned with the present invention and whose contents are incorporated herein by reference.

The position of the magnetic sensor 30 relative to the fiducial mark and target volume may be determined during an initial calibration or initialization procedure, possibly using a so-called phantom representing the target volume. Generally, what is required is the position of the radiation detector 28 relative to the target volume. Although, as described above, this position could be determined with reference directly to the fiducial mark, it could be determined instead with reference to a separate magnetic field sensor placed at a reference point on the patient, for example, upon a visual reference mark e.g. a fiducial mark in the form of a tattoo. The computer 24 might then use the calibration information with the instant position information received from the electronic interface unit 22 to determine the position of the magnetic sensor 30, and hence that of the radiation detector 28, relative to the target volume, taking into account the predetermined distance between the radiation detector and the magnetic sensor.

Typically, the radiotherapy treatment proceeds as follows:

1. It is agreed between the physician and the patient that the patient will receive radiotherapy treatment.

2. Anatomical data is collected.

3. CT or other radiological and/or ultrasound technique is used to define the position, size and shape of the tumour, which may vary with time, entailing 4-dimensional acquisition, i.e., x, y, z, time), and a fiducial mark (e.g., a gold marker or tattoo) applied to the patient as a reference point in the image.

4. Based upon clinical practice, the treatment plan for the delivery of radiation is defined. This includes the number of treatments, the radiation type and the dose which will be delivered to the tumour. As mentioned hereinbefore, although it is important to try and fully irradiate the tumour, it is also important not to irradiate sensitive organs near the tumour. Given the need to eradicate the tumour, if there is uncertainty, the physician may tend to irradiate more rather than less than the target volume, so it is important to establish the boundaries of the tumour accurately.

5. The three-dimensional dose distribution on and/or in the patient anatomy is calculated with reference to the anatomical data (see point 2).

6. The treatment plan is transferred to the treatment unit.

7. The patient is positioned accurately on the treatment bed, with reference to the isocenter 40 and, hence, the radiation source and, where applicable, its locus of movement. Usually, such positioning is facilitated by the fiducial marks on the patient's body.

8. The dosimeter 20 will then be positioned in or on the patient and initialized. As mentioned previously, the magnetic field generator 36 will be located at such a spacing that the magnetic field strength will be adequate in the vicinity of the magnetic field sensor 30.

9. The radiation dose is delivered.

10. The dosimeter radiation detectors are read to determine the radiation dose received.

11. The position of each radiation detector with respect to time is determined using the data from the magnetic tracking system.

12. The dose readings and their positions are compared with the initial treatment plan and the need for treatment adjustment may be assessed.

Generally, the microBIRD™ system will provide an accurate indication of the position of each MOSFET radiation detector 28 in the dosimeter 20. Additional measurements may be made using X-Ray or ultrasound.

Figure 3A:
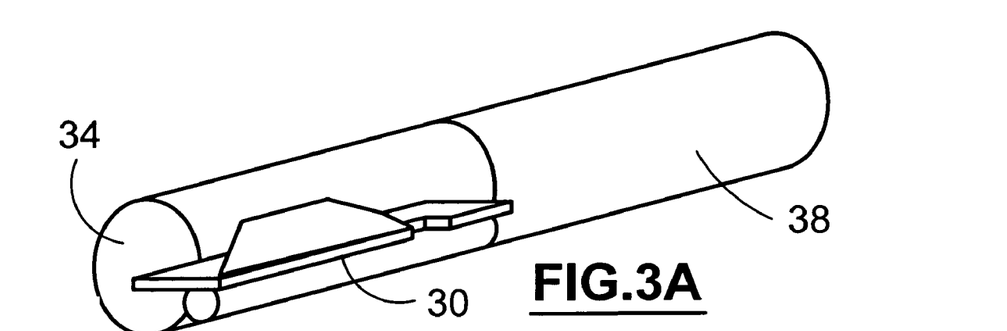
FIGS. 3A and 3B are schematic perspective views of a dosimeter having a radiation detector, a magnetic position sensor and a wireless transmitter device.
Figure 3B:
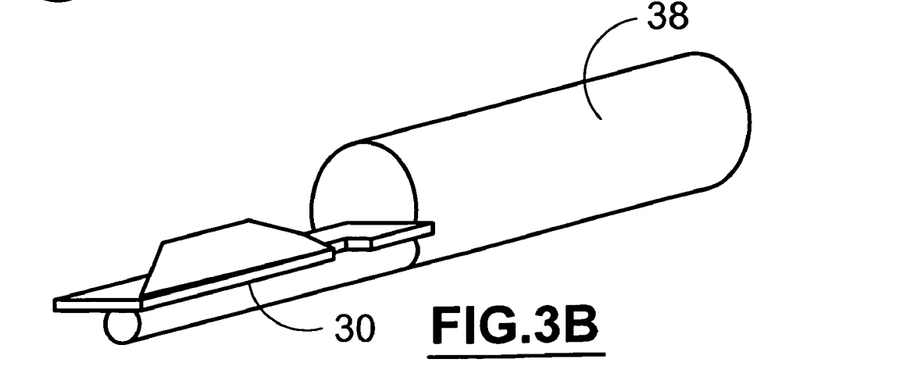

As is known, the dosimeter 20 may additionally comprise a radio-opaque marker visible under X-rays, allowing absolute localization using X-ray imaging techniques with respect to a radiation source Where the dosimeter 20 comprises a flexible printed circuit strip 34 with the detector(s) 28 and sensor 30 at one end, it is generally desirable to minimize the number of conductors in the strip 34 so that it can be inserted into a narrow catheter. It is envisaged, therefore, that the signals from the radiation detector 28 and the magnetic field sensor 30 might be combined, for example time-division-multiplexed, using a suitable circuit or device at that end of the strip 34 and separated out, for example time-division-demultiplexed, by the electronic interface unit 22. Alternatively, the conductors could be dispensed with entirely and replaced by a wireless link. In such an embodiment, a wireless transmitter 38 would be incorporated into the dosimeter 20, as shown in FIGS. 3A and 3B, and the interface electronics unit 22 would have a complementary wireless receiver (not shown). It will be appreciated that, where the dosimeter probe 20 is to be placed outside the patient's body, the wireless link could be optical. If the dosimeter probe 20 were to be placed inside the patient's body, however, the wireless link would preferably be a radio frequency link. It would also be viable for either of the detector and the sensor to be connected using wires or wirelessly.

An advantage associated with the use of a magnetic tracking system, particularly the microBIRD™ system, to track the movement of the sensor and determine the position of the radiation detector(s) is that the equipment used for radiation therapy necessarily has little or no magnetic material, so the effects of extraneous magnetic fields or magnetic materials upon the accuracy of the magnetic tracking system are likely to be insignificant.

In the dosimeter 20 illustrated in FIGS. 2A, 2B, 3A and 3B, the radiation detector 28 and the magnetic field sensor 30 are effectively co-located at the end of the dosimeter 20. It should be noted, however, that they could be separate and placed a predetermined, accurately known distance apart. This might be especially appropriate where several radiation detectors are provided in an array, as disclosed, for example, in US published patent application number 20060027756 (supra). With such a two- or three-dimensional sensor array, a single magnetic sensor 30 could be provided, with the position of each radiation detector predetermined, three-dimensionally, relative to the magnetic sensor 30, and this information loaded into the computer 24 (or the reader interface electronics 22).

Figure 4:
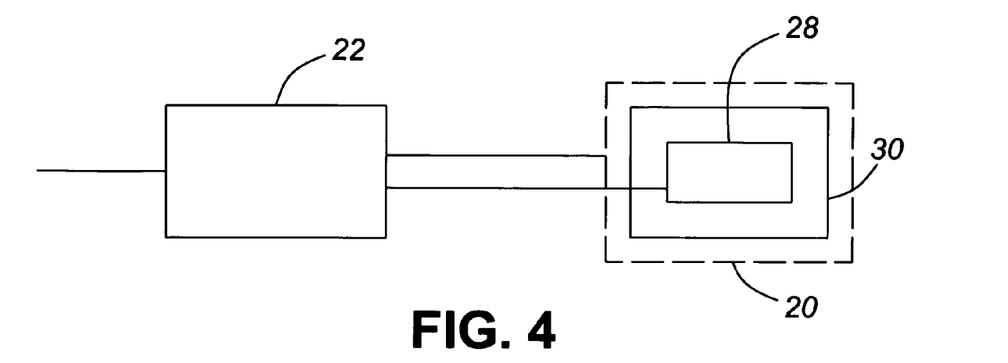
FIGS. 4, 5, 6 and 7 are simplified schematic illustrations of alternative configurations of dosimeters and associated interface devices.
Figure 5:
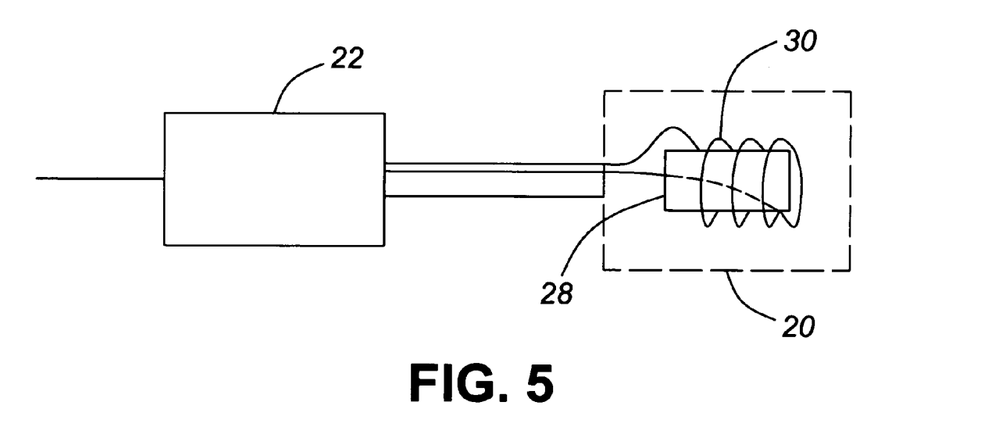

In the dosimeter probe 20 shown in FIGS. 2A to 3B, the radiation detector 28 and the magnetic field sensor 30 are disposed upon opposite sides of a substrate. Alternative configurations are envisaged, however. For example, as illustrated in FIG. 4, the radiation detector 28 may be within the magnetic field sensor 30. More specifically, the magnetic field sensor 30 may comprise a helical coil wrapped around the MOSFET detector 28, as illustrated in FIG. 5.

It is preferable for the or each radiation detector 28 to exhibit isotropic sensitivity to radiation from different directions, as disclosed in U.S. Pat. No. 6,614,025, and for the magnetic location sensor 30 to be spaced from the radiation detector 28 so as not to substantially interfere with the isotropic sensitivity of radiation detector. It would be possible, however, to use a radiation detector which was not isotropic and compensate for angular variations in sensitivity on the basis of orientation information from the position tracking system if, as is possible, the tracking system tracks not only position but also orientation of the sensor.

It should be appreciated that, although the above-described embodiments preferably use a MOSFET radiation detector 28, or another type of insulated gate field effect transistor (IG-FET), a floating gate MOSFET, the radiation detector could be of a different kind, a diode, a thermoluminescent dosimeter (TLD) detector, a scintillator, an OSL (Optically stimulated luminescence) dosimeter, an ion chamber, a doped silica glass or polymer optical fiber or other suitable device, as appropriate to the particular application and with appropriate modification other elements of the system, as necessary.

The MOSFET dosimeter has a threshold voltage sensitive to radiation, which can be used to quantify the radiation dose. The MOSFET dosimeter can be a single MOSFET device or optionally combined with a temperature sensor to correct for threshold voltage fluctuations due to temperature variation. It can be composed of two MOSFETs (dual-MOSFET) used in combination on a similar substrate to compensate for temperature induced voltage fluctuations as disclosed, for example as disclosed in U.S. Pat. No. 4,678,916 (Thomson). The diode and the ion chamber measure current or charge created by irradiation. The TLD, OSL, and scintillation detectors generate light output on irradiation to measure dose.

Although the above-described embodiments use a visual reference mark and/or the isocentre 40, or other fixed datum, for initial localization of the system, it is envisaged that other appropriate reference or alignment systems known to those skilled in this art could be used.

The radiation and position dosimeter 20 may be located at any accessible point of a human or animal patient or non-living material. Such accessible points may be on the surface of the patient, or inside the patient and accessed by means of a natural orifice, or by means of a surgical opening. The therapy methods may include both teletherapy and those described as Brachytherapy. Another accessible point could be located at a distance from the patient and used for radiation protection applications.

The radiation detector 28 may measure any part of the ionizing radiation spectrum, including X-rays, gamma rays, electrons, protons or other particulate radiation, subject to any limitations imposed by the subject which, as stated above, may be living or non-living.

The radiation detector 28 may have any appropriate angular reception sensitivity for the radiation dose to be measured. For example, it may be isotropic, and have the same sensitivity to radiation from all directions, for example as disclosed in U.S. Pat. No. 6,614,025 (Thomson et al.). Alternatively, by appropriate design of the radiation and position dosimeter 20, it is possible to shape the radiation reception (sensitivity) angles so that the device is anisotropic i.e., its sensitivity in some directions is greater than its sensitivity in other directions. This greater sensitivity could have advantages in such situations such as ensuring that the detector in a very large patient was still able to measure the radiation dose. In this case, the use of a positioning device which provides greater sensitivity over certain directions is desirable.

Advantageously, because dosimeters embodying the present invention integrate a radiation detector and a position sensor to facilitate the measurement of radiation and the position at which the radiation is measured, suitable selection of these detectors and sensors allows a small volume dosimeter capable of precise dose measurement to be combined with a position tracking system capable of accurately determining the position and orientation of the radiation detector(s) relative to the target volume in real time. This is in contrast to previously known dosimeters where the focus primarily was upon improving their performance and portability without consideration of their location on the surface of the patient or inside the patient body. The combined sensing of the location using a magnetic field tracking system and the radiation dose at that location provides new applications.

In Low Dose Rate (LDR) Brachytherapy, the value of providing not only the radiation dose but also the position of a (MOSFET) detector inside the urethra for predicting urinary complications has been demonstrated, specifically for a dosimeter having an array of detectors, as disclosed in US published patent application number 20060027756. In High Dose Rate (HDR) Brachytherapy, due to the nature of dose delivery (high dose in a short period of time) it is important to perform in vivo dosimetry in a well-defined location in order to avoid dose misadministration. Embodiments of the invention combined with Image Guided Radiation Therapy (IMRT) provide accurate information about the measured dose correlated with patient anatomy.

It should be noted that dosimeters embodying the present invention could be used to measure dose during diagnostic procedures in nuclear medicine and radiology. This could be especially of value when pediatric patients are involved and the radiation dose is important. This is also of value for patients undergoing interventional angiography procedures (X-rays, Fluoroscopy) to determine dose at specific locations.

It is envisaged that the detectors might be arranged in a two-dimensional array, especially if placed in a phantom, and the output means them may perform corresponding two-dimensional processing of the position signals, and display the corresponding radiation doses in a corresponding two-dimensional representation of the array. Similarly, if the array is three-dimensional, the output means may perform corresponding three-dimensional processing of the position signals, and display the corresponding radiation doses in a corresponding three-dimensional representation of the array. Likewise, where the detectors are arranged in a linear array, the output means may process the position signals to provide and display a corresponding linear representation of the doses and their respective positions. In these configurations, the array of detectors may be provided on a rigid or a flexible supporting medium.

Figure 6:
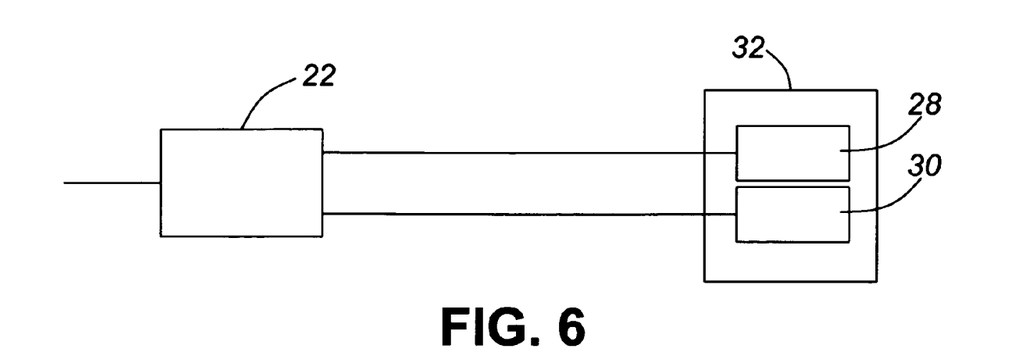
Figure 7:
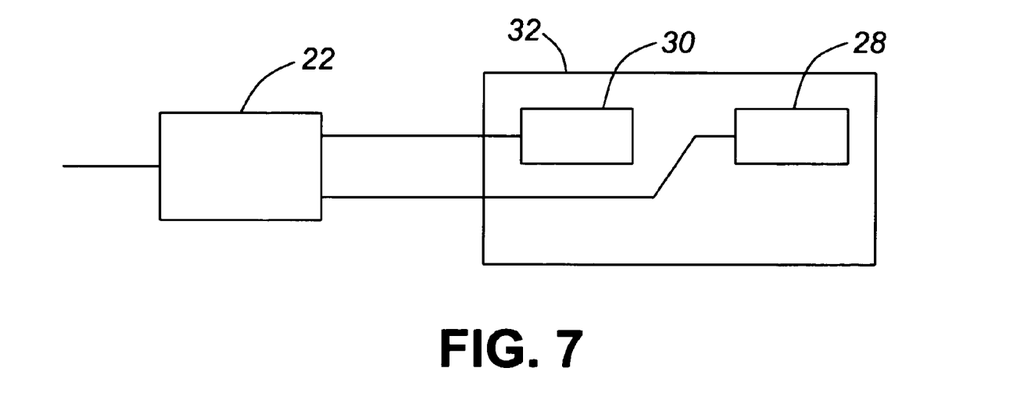

As mentioned above, the three-dimensional spatial relationship between the radiation detector 28 and the magnetic sensor 30 must be predetermined accurately during manufacture, or during use, because this spatial relationship must be taken into account when determining the position of the radiation detector 28 based upon information about the position of the magnetic sensor 30. A magnetic position sensor 30 and a radiation sensor 28 may mounted on opposite sides of a substrate 32 as shown schematically in FIGS. 2 to 4, with the two sensors 28, 30 effectively co-located, to enable the position and orientation of the radiation sensor to be determined accurately relative to the magnetic position sensor. As shown in FIG. 5, in another configuration, a magnetic position sensor 30 may take the form of a helical coil surrounding the radiation sensor 30. Alternatively, a dosimeter may comprise a magnetic position sensor 30 and a radiation detector 28 mounted side by side on a substrate 32 separated laterally by a predetermined distance as shown in FIG. 6. In another configuration, as shown schematically in FIG. 7, a magnetic position sensor 30 may be mounted on a substrate of the dosimeter offset longitudinally by a predetermined distance from the radiation detector 28. The latter arrangement may be preferred when an isotropic response of the radiation detector is desired in specific directions.

Where the dosimeter comprises an array of radiation detectors 28 is provided on a substantially rigid support or substrate, the relative position and orientation of each radiation sensor may be determined reliably relative to one magnetic position sensor 30.

Where an array of detectors is provided on a flexible support, advantageously the dosimeter comprises more than one magnetic position sensors 30 to enable the position of the radiation detectors 28 to be determined more accurately when the support flexes. If required, the dosimeter may comprise multiple magnetic sensors 30, each radiation sensor 28 of an array being located close enough to a respective magnetic sensor 30 to enable the spatial relationship, i.e. the position and orientation of each radiation detector 28 to be determined with the desired accuracy. Nevertheless, as mentioned above, where isotropic response of the radiation detector 28 is important it may be desirable that each radiation detector 28 and an associated magnetic position sensor 30 are spaced apart by a predetermined distance, for example as shown FIG. 7, or alternatively compensation for anisotropic response of the radiation detector 28 may be provided by known methods.

An additional stand-alone magnetic position sensor 30 at a reference point (i.e. not combined with the dosimeter) may be used as a position reference for a dosimeter comprising a position sensor 30 associated with the radiation detector 28 to determine movement relative to the reference point.

The above-described embodiments of the invention can provide an accurate measurement of both the dose and the position at which the dose was measured, facilitating comparison of the actual dose at a particular position/location with the treatment plan.

It is also envisaged, that embodiments of the invention could provide a "gating" system whereby radiation treatment is given when the position of the patient relative to the radiation source is within certain tolerances. Such gating is normally used where the movement (breathing) is regular and repeatable. In such a case, the computer 24 would track the movement as before but interface with the external beam radiation therapy equipment to control the beam according to the movement of the target. Thus, the system may provide real time dose and location monitoring signals for controlling the radiation beam manually or automatically, for example to switch the beam off when threshold dose or location limits are reached.

This would be much simpler than, for example, the procedure disclosed in United States published patent application number 2006/0074292 which involves CT imaging and complicated mathematical processing to predict dose distribution taking motion into account.

Because embodiments of the invention measure the actual dose received at the specified locations, and do so in a relatively simple manner, it is envisaged that they might be used to complement or even supplant known techniques for tracking movement of the target during therapy.

Where movements of the dosimeter probe and/or target volume are not regular, such as those caused by shifting of the patient to improve comfort, or the natural movement of internal organs, embodiments of the present invention advantageously may provide valuable information on the changes in position of the measurement points on the surface of the patient's body, or internally.

Embodiments of the invention may be employed with so-called phantoms, which allow simulation of the effect of radiation within organs. Such phantoms are usually made of synthetic plastics material in the appropriate shapes to simulate a single or several organs. They are used as a test device to measure the expected radiation doses within a patient.

It will be appreciated that, although the above-described embodiments are used for radiotherapy applications, the invention comprehends dosimeters and associated dosimetry methods used to validate the performance of other medical radiation systems to measure the radiation dose and its position, and, if desired, compare with the expected or specified dose.

For example, the dosimetry apparatus may comprise a dosimeter 20 that can be attached to a movable device so the dosimeter is movable to scan a space such as a water tank phantom, in a predefined manner in linear (1-D), planar (2-D) and volumetric (3-D) patterns, and display radiation doses mapped to their respective positions at defined times.

In embodiments of the invention, the dosimeter may have means for applying it to the surface of a patient; or be adapted for application inside a natural orifice in a patient such as the mouth, rectum, urethra, nose; or for application inside a patient in an artificial orifice such as may be made by a hollow needle; or be provided with or adapted for insertion into an artificial body part (phantom). As mentioned above, a dosimeter/position sensor having small dimensions may fit inside small diameter catheters (D<2 mm) that can be inserted inside tumors or body cavities for dose and position determination during irradiation.

As is known, a dosimeter in the form of a small diameter assembly can be used on the surface of materials to estimate dose at different depths. Use of a dosimeter having both a magnetic position sensor and a radiation sensor allows for dose estimation at different depths in a given volume with simultaneous determination of dose and position. The dosimeter may be covered with partial or full build-up materials (metals, alloys or non-metals) of any shape, with preference to hemispherical shape at a body surface allowing accurate and simultaneous dose and position determination on the skin surface or at the tumor volume. In this context, a build-up material is preferably made of a metal alloy such as brass with no iron content (non-ferrous metal) or other non-magnetic materials, to avoid interfering with the magnetic positioning system. A magnetic positioning system based on a DC magnetic field is also preferred to avoid eddy current effects which may be induced in metals by AC magnetic fields.

An advantage of embodiments of the invention which monitor the radiation level signal and position signal with respect to time is that they can be interfaced to, specifically synchronized with, other equipment to allow correlation between radiation level reading and, for example, an image of the target.

Although embodiments of the invention have been described and illustrated in detail, it is to be clearly understood that the same is by way of illustration and example only and not to be taken by way of the limitation, the scope of the present invention being limited only by the appended claims.

What is claimed is:

1. Dosimetry apparatus for determining radiation dose applied to a target during a radiotherapy/surgery session comprises:

a dosimeter configured for location in or adjacent said target during said session, output means coupled to the dosimeter, and magnetic field generating means, the dosimeter comprising at least one radiation detector means and at least one magnetic field sensor means located a predetermined distance apart, the magnetic field generator being operable to establish a magnetic field encompassing said magnetic field sensor during/throughout said radiotherapy/surgery session, the radiation detector means being arranged to sense ionizing radiation and provide a corresponding radiation level signal, the magnetic field sensor means being responsive to movement thereof relative to the magnetic field to provide a corresponding position sensor signal, and the output means being arranged to process both the radiation level signal and the position sensor signal and, in dependence thereupon, provide an indication of both the level of a radiation dose detected by the radiation detector and the location at which the dose was measured.

2. Dosimetry apparatus according to claim 1, wherein the output means monitors the radiation level signal and the position sensor signal with respect to time and correlates according to time to obtain said level of a radiation dose and the location at which the dose was measured.

3. Dosimetry apparatus according to claim 2, wherein the output means monitors the position sensor signal continuously and the radiation level periodically.

4. Dosimetry apparatus according to claim 2 wherein the output means provides real time dose and location monitoring signals for gating of a radiation source with respect to at least one of threshold dose and location limits.

5. Dosimetry apparatus according to claim 1, wherein the magnetic field sensor means comprises a plurality of coils having axes extending in different directions, and movement of the coils relative to said magnetic field generates the corresponding sensor signals, the output means including processing means for processing the sensor signals to obtain direction and distance of movement of the magnetic field sensor and therefrom instant position of the radiation detector.

6. Dosimetry apparatus according to claim 1, wherein the radiation detector means comprises a plurality of radiation detectors spaced apart relative to each other and each having a predetermined spacing from the magnetic field sensor means.

7. Dosimetry apparatus according to claim 6, wherein the radiation detectors are arranged in a two-dimensional array and the output means performs corresponding two-dimensional processing of the position sensor signals, the output means further comprising means for displaying the corresponding radiation doses in a corresponding two-dimensional representation of the array.

8. Dosimetry apparatus according to claim 6, wherein the radiation detectors are arranged in a three-dimensional array and the output means performs corresponding three-dimensional processing of the position signals, the output means further comprising means for displaying the corresponding radiation doses in a corresponding three-dimensional representation of the array.

9. Dosimetry apparatus according to claim 6, wherein the detectors are arranged in a linear array and the output means processes the position signals to provide and display a corresponding linear representation of the doses and their respective positions.

10. Dosimetry apparatus according to claim 1, wherein one of the radiation detector means and the magnetic field sensor means is connected to conductors for connection to the output means.

11. Dosimetry apparatus according to claim 1, wherein both the radiation detector means and the magnetic field sensor means are connected to conductors for connection to the output means.

12. Dosimetry apparatus according to claim 1, wherein one of the radiation detector means and the magnetic field sensor means is connected by conductors and the other is connected wirelessly.

13. Dosimetry apparatus according to claim 1, wherein the output means is operable to track movement of the sensor means relative to a spatial reference.

14. Dosimetry apparatus according to claim 13, wherein the spatial reference comprises one or more fiducial marks on or adjacent the target.

15. Dosimetry apparatus according to claim 14, wherein the spatial reference comprises an isocentre of apparatus sourcing the radiation.

16. Dosimetry apparatus according to claim 1, wherein the output means further comprises display means for displaying simultaneously both radiation doses and respective locations thereof.

17. Dosimetry apparatus according to claim 1 wherein the dosimeter is movable to scan a space in a predefined manner in linear (I-D), planar (2-D) and volumetric (3-D) patterns, and display radiation doses mapped to their respective positions at defined times.

18. A method of measuring both radiation dose and a position at which the dose was measured, the method using a dosimeter having a radiation detector and a magnetic position sensor a predetermined distance apart, and magnetic field generating and detecting means, the method comprising the steps of:
positioning the radiation detector and the magnetic position sensor at known distance relative to fiducial marker and establishing the position of the sensor as a datum,
positioning the radiation detector at a desired position at which to measure radiation dose during radiation therapy,
determining the position of the magnetic field sensor,
measuring the radiation dose acquired by the radiation detector over a prescribed period of time, and
correlating the measured radiation dose with the position of the magnetic sensor thereby to determine the position at which the dose was measured.

19. A method according to claim 18, wherein the radiation level signal and the position sensor signal are each monitored with respect to time and correlated according to time to obtain said level of a radiation dose and the location at which the dose was measured.

20. A method according to claim 19, wherein the position sensor signal is monitored continuously and the radiation level periodically.

21. A method according to claim 19, wherein signals from the magnetic position sensor and radiation detector are correlated according to time, and with at least one of a physiological signal from a patient undergoing therapy and a signal from other monitoring equipment, and further comprising generating gating signals for controlling the dose delivered to the target.

22. A method according to claim 18, wherein the dose and its position are measured at intervals throughout a planned therapy session and the treatment plan adjusted to compensate for variations of the measured dose at a particular position with respect to the planned dose.

23. A method according to claim 18 wherein the radiation detector sensitivity is anisotropic, and comprising the step of compensating for angular variations in sensitivity on the basis of orientation information derived from the magnetic position sensor.

24. A method according to claim 18, further comprising the step of determining position relative to a second magnetic field sensor placed at a reference point.

25. A dosimeter having a radiation detector and a magnetic position sensor a predetermined distance apart and means for connecting respective outputs ports of the radiation detector and the magnetic field sensor to external reading means for extracting signals from the radiation detector and magnetic field sensor for processing to determine a radiation level measured by the radiation detector and its position when the radiation level was measured.

26. A dosimeter according to claim 25, wherein the radiation detector and the magnetic position sensor are relatively positioned to allow for substantially isotropic response of the radiation detector.

27. A dosimeter according to claim 26, wherein the radiation detector and the magnetic position sensor are located a predetermined distance apart in a lateral direction with respect to an axis of the dosimeter.

28. A dosimeter according to claim 26, wherein the radiation detector and the magnetic position sensor are located a predetermined distance apart in a longitudinal direction with respect to an axis of the dosimeter.

29. A dosimeter according to claim 25 wherein the radiation detector and the magnetic position sensor are fixed spatially relative to each other.

30. A dosimeter according to claim 25 provided within a catheter.

31. A dosimeter according to claim 25 covered with partial or full build-up materials comprising non-ferrous metals or other non-magnetic materials.

32. A dosimeter according to claim 25, where the radiation sensor is one of a MOSFET radiation detector, a floating gate MOSFET, an insulated gate field effect transistor (IGFET), a diode, a thermoluminescent dosimeter (TLD) detector, a scintillator, an OSL (Optically stimulated luminescence) dosimeter, an ion chamber, a doped silica glass or polymer optical fiber or other suitable device.

33. A dosimeter according to claim 25 wherein the radiation sensor is one of a single MOSFET, a single MOSFET with a temperature sensor for noise compensation, and a dual MOSFET device having inherent temperature and noise compensation.

34. A dosimeter according to claim 25 further comprising a radio-opaque marker.

35. A dosimeter according to claim 25 comprising an array of radiation sensors provided on a flexible support, and a plurality of magnetic positioning sensors, each radiation sensor being located within a predetermined distance of an associated one of the plurality of magnetic positioning sensors.

36. A dosimeter according to claim 25 wherein the radiation sensor and a magnetic sensor are provided on a flexible substrate comprising multilayer conducting tracks.

* * * * *